United States Patent
Ammar et al.

(10) Patent No.: US 12,153,027 B1
(45) Date of Patent: Nov. 26, 2024

(54) TUNABLE LASER SPECTROSCOPY MEASUREMENT OF C13 ETHANE

(71) Applicant: SCHLUMBERGER TECHNOLOGY CORPORATION, Sugar Land, TX (US)

(72) Inventors: Mahdi Ammar, Clamart (FR); Dariusz Strapoc, Clamart (FR); Jerome Breviere, Taverny (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 18/720,294

(22) PCT Filed: Jun. 29, 2023

(86) PCT No.: PCT/US2023/069324
§ 371 (c)(1),
(2) Date: Jun. 14, 2024

(87) PCT Pub. No.: WO2024/006875
PCT Pub. Date: Jan. 4, 2024

(30) Foreign Application Priority Data

Jun. 29, 2022 (EP) .................................. 22305942

(51) Int. Cl.
*G01N 30/74* (2006.01)
*B01D 53/02* (2006.01)
(Continued)

(52) U.S. Cl.
CPC ........... *G01N 30/74* (2013.01); *B01D 53/025* (2013.01); *G01N 30/52* (2013.01);
(Continued)

(58) Field of Classification Search
CPC .... G01N 30/74; G01N 30/52; G01N 33/0027; G01N 2030/025; G01N 2030/522; B01D 53/025; B01D 2257/7022
See application file for complete search history.

(56) References Cited

U.S. PATENT DOCUMENTS

| 8,810,794 B2 | 8/2014 | Breviere |
| 9,671,381 B2 | 6/2017 | Karoum |

(Continued)

FOREIGN PATENT DOCUMENTS

| CA | 2660429 C | 7/2016 |
| WO | 2021069800 A1 | 4/2021 |

OTHER PUBLICATIONS

Zare et al., "High-precision optical measurements of 13C/12C isotope ratios in organic compounds at natural abundance", Proceedings of the National Academy of Science, 2009, vol. 106, No. 27, pp. 10928-10932.
(Continued)

*Primary Examiner* — Tarun Sinha
(74) *Attorney, Agent, or Firm* — Jeffrey D. Frantz

(57) ABSTRACT

An apparatus for making isotopic ethane measurements of a gas sample includes a tunable infrared laser configured to emit an infrared laser beam; an infrared sensor configured to receive the infrared laser beam; a gas cell deployed in a path between the tunable infrared laser and the infrared sensor such that the infrared laser beam passes through the gas cell, the gas cell configured to receive the gas sample; and a controller configured to evaluate the received infrared laser beam to estimate a ratio of C13 ethane to C12 ethane in the gas sample.

14 Claims, 10 Drawing Sheets

(51) Int. Cl.
    *G01N 30/52*    (2006.01)
    *G01N 33/00*    (2006.01)
    *G01N 30/02*    (2006.01)

(52) U.S. Cl.
    CPC . *G01N 33/0027* (2013.01); *B01D 2257/7022* (2013.01); *G01N 2030/025* (2013.01); *G01N 2030/522* (2013.01)

(56) References Cited

U.S. PATENT DOCUMENTS

2004/0164237 A1    8/2004    Jones
2012/0298868 A1\*  11/2012   Massick ................ G01N 21/39
                                                                             250/339.13
2022/0364984 A1\*  11/2022   Kääriäinen ............. G01J 3/433

OTHER PUBLICATIONS

Search Report and Written Opinion of International Patent Application No. PCT/US2023/069324 issued Oct. 17, 2024; 11 pages.

\* cited by examiner

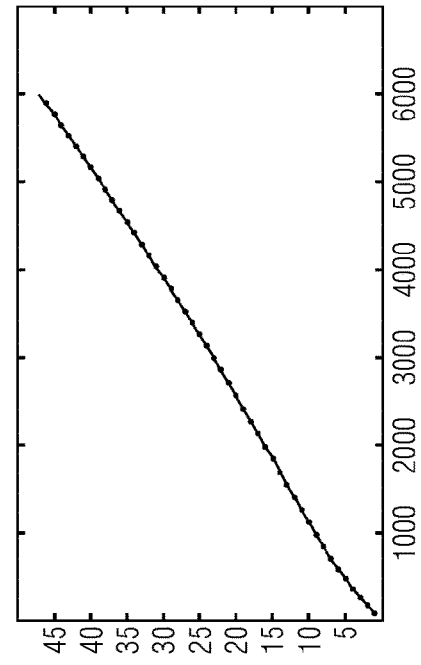
FIG. 7B
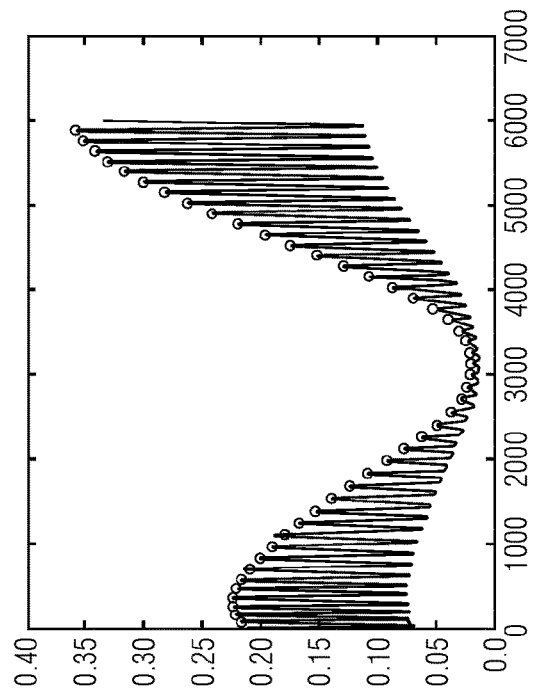
FIG. 7A
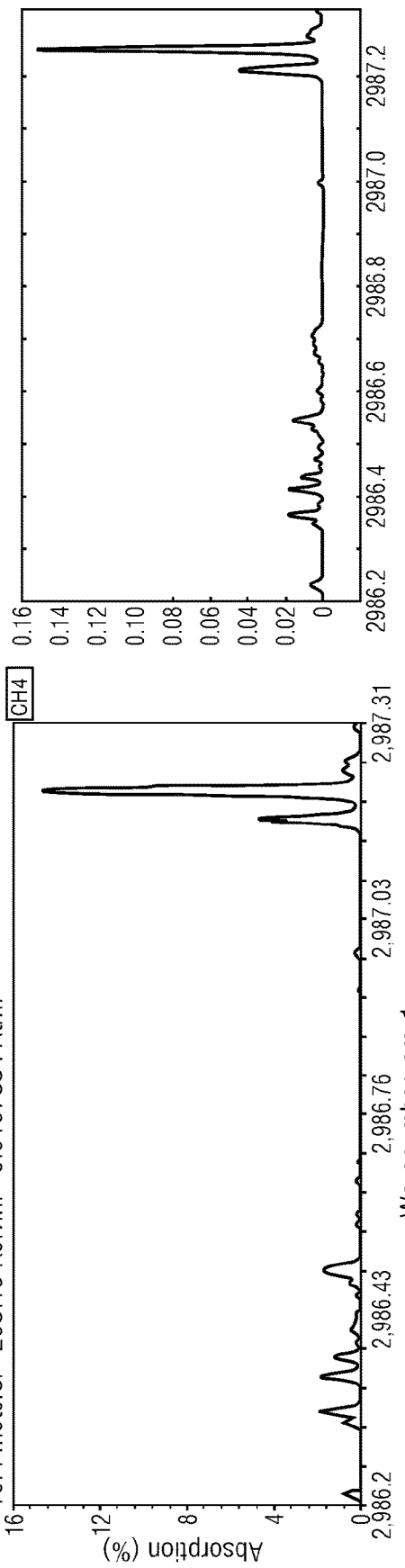
FIG. 8B
FIG. 8A

TUNABLE LASER SPECTROSCOPY MEASUREMENT OF C13 ETHANE

CROSS REFERENCE TO RELATED APPLICATIONS

This application is the National Stage Entry of International Application No. PCT/US2023/069324, filed Jun. 29, 2023, which claims priority to European Patent Application No. EP22305942.9, which was filed on Jun. 29, 2022, and each of the above applications is incorporated herein by reference in its entirety.

BACKGROUND

Formation gas composition is commonly measured while drilling oil and gas wells to enable geologists to characterize reservoir fluid composition while drilling. On-site gas chromatography (GC) is commonly combined with a flame ionization detector (FID) to make such measurements. While GC and FID sensors can provide accurate measurements, they are not well suited to continuous gas monitoring owing to the long GC cycle time (e.g., about 5 minutes).

There is currently no suitable known method for making on-site measurements of an isotopic ethane ratio. U.S. Pat. No. 8,810,794 discloses a cavity enhanced spectroscopy method for measuring an isotopic ratio of methane (C1) in the near infrared spectral region. However, the disclosed method is not suitable for measuring heavier hydrocarbons, such as ethane (C2) and propane (C3), which are used for geochemistry evaluation in the oil and gas exploration industry.

A common approach used in a laboratory environment to measure C1 to C3 isotope ratios is based on the separation and measurement of these hydrocarbons, using a gas chromatograph (GC), high-temperature combustion oven, and isotope ratio mass spectrometry (GC-IRMS). With commercial GC-IRMS technology, chromatography analysis is often performed using a general-purpose gas chromatograph that is not optimized for on-line real time measurement. Additionally, the combustion oven tends to be easily broken and prone to leaks at high operating temperatures (~900° C.).

This conventional laboratory approach is not suitable for deployment in the field due to its complexity, low reliability, and high cost. The long GC cycle-time (about 5 minutes) further constrains continuous gas measurement at the wellsite, where the industry is aiming at having the best vertical logging resolution possible. There is a need in the industry for making rapid (e.g., less than 1 minute interval) measurements of the isotopic ratio of naturally occurring ethane.

BRIEF DESCRIPTION OF THE DRAWINGS

For a more complete understanding of the disclosed subject matter, and advantages thereof, reference is now made to the following descriptions taken in conjunction with the accompanying drawings, in which:

FIGS. 7A and 7B (collectively FIG. 7) depicts absorbance as a function of wavelength calculated and linearized by means of a 2.54 cm long Germanium etalon with a free spectral range (FSR) of 1.44 GHz (7A) and a calibration model used to convert spectrum channels (or data points) to the corresponding wavenumbers (7B).

FIGS. 8A and 8B (collectively FIG. 8) depict theoretical (8A) and experimental (8B) methane absorption spectra.

DETAILED DESCRIPTION

Embodiments of this disclosure include apparatuses and methods for making isotopic ethane measurements of a gas sample. In one example embodiment, a disclosed apparatus includes a tunable infrared laser configured to emit an infrared laser beam; an infrared sensor configured to receive the infrared laser beam; a gas cell deployed in a path between the tunable infrared laser and the infrared sensor such that the infrared laser beam passes through the gas cell, the gas cell configured to receive the gas sample via a gas inlet and expel the gas sample via a gas outlet; and a controller configured to evaluate the received infrared laser beam to estimate at least a ratio of C13 ethane to C12 ethane in the gas sample. In certain advantageous embodiments, the gas cell may include a hollow wave guide and the apparatus may further include a GC column configured to isolate an ethane sample from the gas sample and inject the ethane sample into the hollow wave guide.

Example methods for making isotopic ethane measurements of a gas sample may include introducing the gas sample to a gas cell; scanning a tunable infrared laser between first and second wavelengths; measuring a spectrum corresponding to the infrared laser scan; identifying first and second absorption peaks in the measured spectrum corresponding to C13 ethane and C12 ethane; computing first and second amplitudes of the first and second absorption peaks; and computing a ratio of the first and second amplitudes to estimate the ratio of C13 ethane to C12 ethane in the gas sample.

Figure 1:
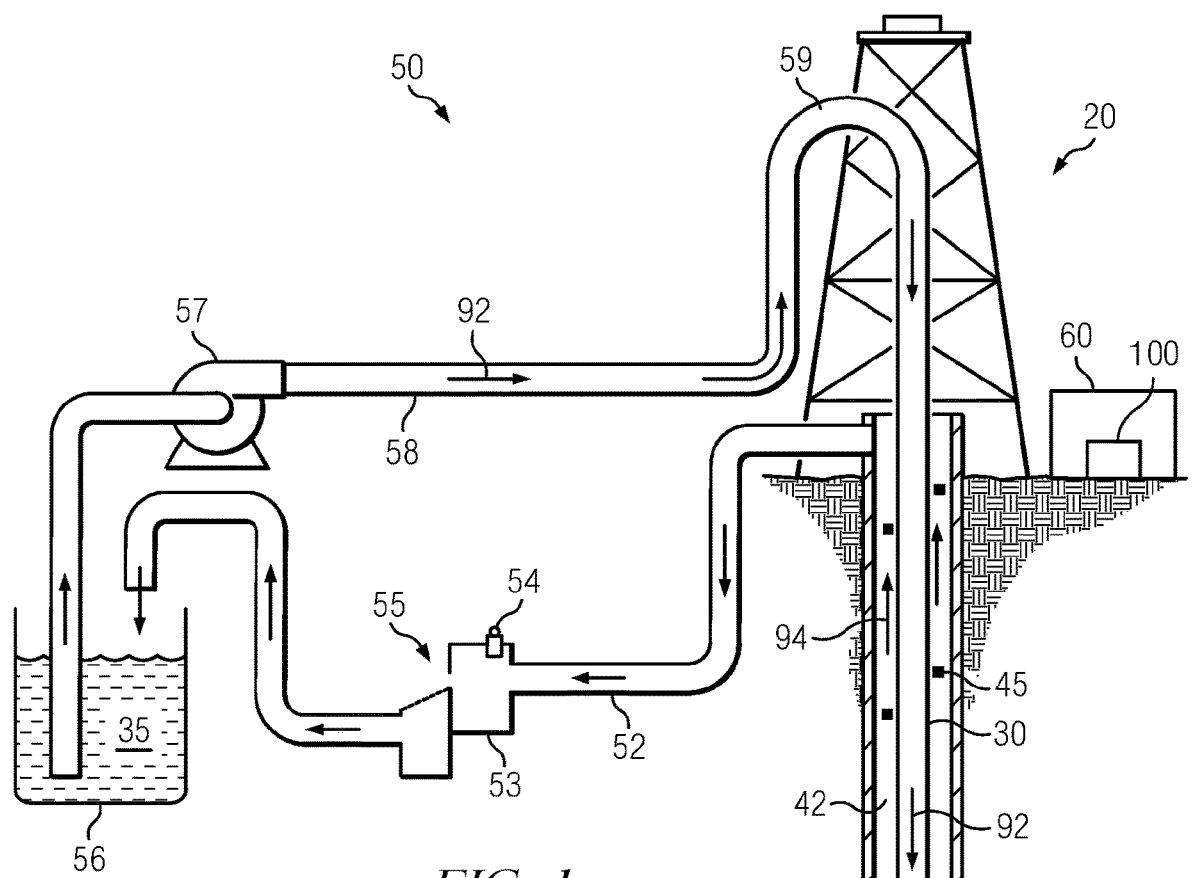
FIG. 1 depicts an example drilling rig including an apparatus for measuring an isotopic ratio of naturally occurring ethane gas.

FIG. 1 depicts an example drilling rig 20 including a gas chromatography apparatus 100 for evaluating formation gas composition. The drilling rig 20 may be positioned over a subterranean formation (not shown). The rig 20 may include, for example, a derrick and a hoisting apparatus (also not shown) for raising and lowering a drill string 30, which, as shown, extends into wellbore 40 and includes, for example, a drill bit 32 and one or more downhole measurement tools 38 (e.g., a logging while drilling tool or a measurement while drilling tool) in a bottom hole assembly (BHA) above the bit 32. Suitable drilling systems, for example, including drilling, steering, logging, and other downhole tools are well known in the art.

Drilling rig 20 further includes a surface system 50 for controlling the flow of drilling fluid used on the rig (e.g., used in drilling the wellbore 40). In the example rig depicted, drilling fluid 35 is pumped downhole (as depicted at 92), for example, via a conventional mud pump 57. The drilling fluid 35 may be pumped, for example, through a standpipe 58 and mud hose 59 in route to the drill string 30. The drilling fluid 35 typically emerges from the drill string 30 at or near the drill bit 32 and creates an upward flow 94 of mud through the wellbore annulus 42 (the annular space between the drill string and the wellbore wall). The drilling fluid 35 then flows through a return conduit 52 to a mud pit system 56 where may be recirculated. It will be appreciated that the terms drilling fluid and mud are used synonymously herein.

The circulating drilling fluid 35 is intended to perform many functions during a drilling operation, one of which is to carrying drill cuttings 45 to the surface (in upward flow 94). The drill cuttings 45 are commonly removed from the returning mud via a shale shaker 55 (or other similar solids control equipment) in the return conduit (e.g., immediately upstream of the mud pits 56). Formation gases that are released during drilling may also be carried to the surface in the circulating drilling fluid. These gasses are commonly removed from the fluid, for example, via a degasser or gas trap 54 located in or near a header tank 53 that is immediately upstream of the shale shaker 55 in the example depiction. The drill cuttings 45 and gas are commonly examined at the surface to evaluate the formation layers though which the wellbore is drilled.

The disclosed embodiments include methods and systems for estimating (e.g., measuring) a ratio of carbon-13 ethane (referred to herein as C13 ethane) to carbon-12 ethane (referred to herein as C12 ethane) in naturally occurring ethane gas. By naturally occurring, it is meant that the ethane gas originates in the subterranean formation. As is known to those of ordinary skill in the art, formation gas (including ethane) may be released into the wellbore 40 via the drilling process (e.g., crushing the formation rock by the mechanical action of the drill bit) and may also migrate into the wellbore 40, for example, via fractures in the formation rock. Once in the wellbore, the formation gas may be transported to the surface via the drilling fluid (in the upwardly flowing fluid 94). The formation gas may be in solution in the drilling fluid and/or in the form of bubbles and may be sampled in the surface system, for example, via one or more drilling fluid degassers 54 and/or a head space gas probe. The disclosed embodiments are expressly not limited in regards to how the gas is sampled.

With further reference to FIG. 1, drilling rig 20 may further include a testing facility 60 (e.g., a laboratory trailer including one or more instruments suitable for making various measurements of drill cuttings and formation gases in the drilling fluid). The testing facility 60 includes an apparatus 100 (described in more detail below) configured to estimate an isotopic ratio of ethane gas (e.g., a ratio of C13 ethane to C12 ethane). The testing facility 60 may, of course, include numerous other testing instruments known to those of ordinary skill in the industry.

Figure 2:
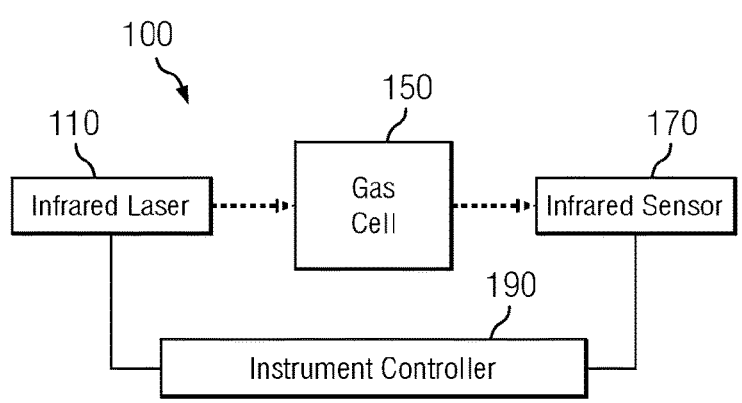
FIG. 2 depicts an example isotopic ratio measurement apparatus.

FIG. 2 depicts one example embodiment of gas testing apparatus 100. In the embodiment depicted on FIG. 2, apparatus 100 includes an infrared laser 110 configured to emit infrared radiation (e.g., an infrared laser beam) and an infrared sensor 170 configured to receive the infrared laser beam. A gas cell 150 is configured to receive a formation gas sample (e.g., via a gas inlet) and is deployed between laser 110 and the sensor 170 such that the emitted radiation passes through the gas sample in the gas cell 150. A controller 190 is configured to process the received infrared radiation to estimate a ratio of C13 ethane to C12 ethane in the gas sample.

Figure 3:
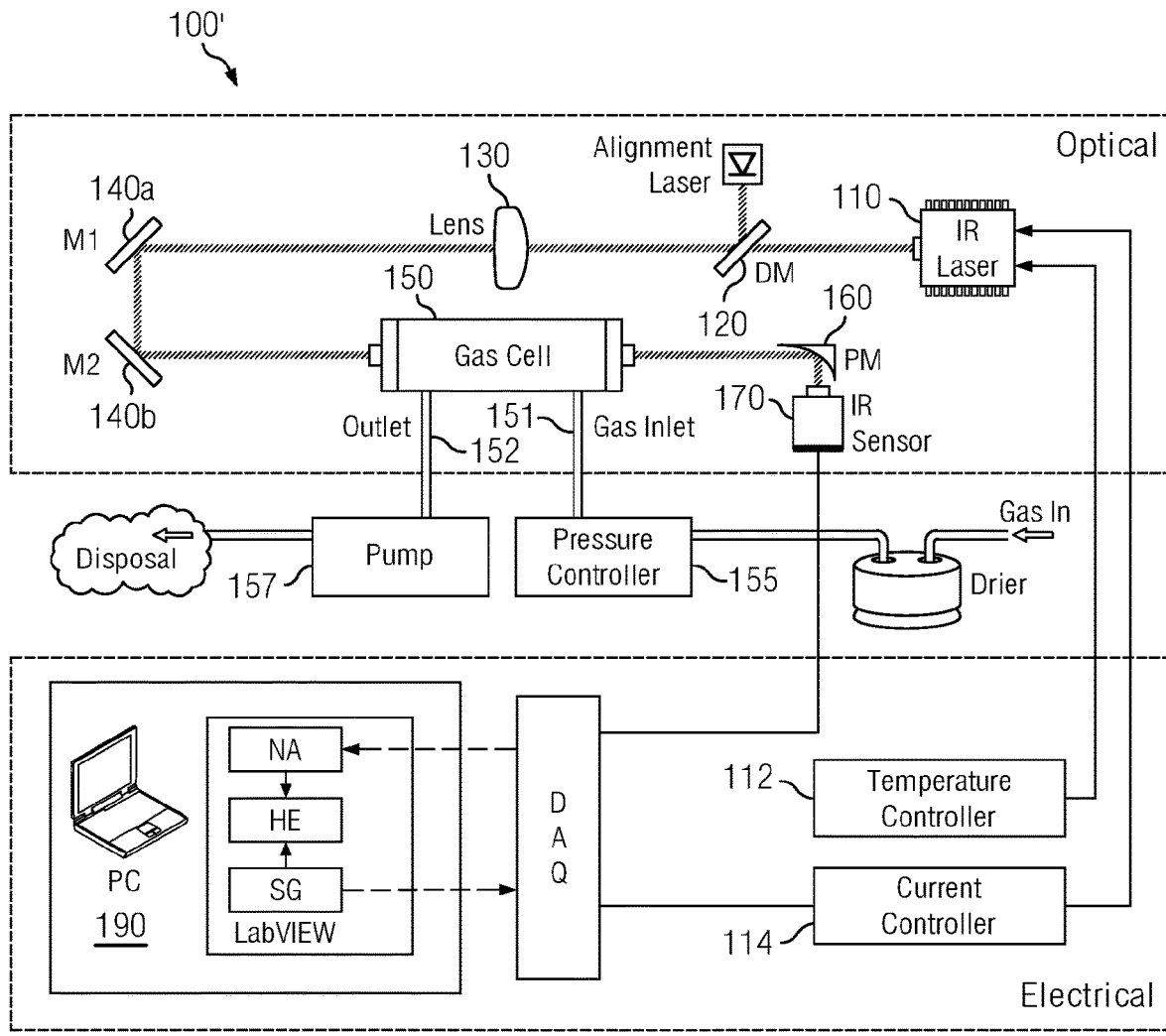
FIG. 3 depicts another example isotopic ratio measurement apparatus.

FIG. 3 depicts another example apparatus 100' for making isotopic ethane measurements. The apparatus 100' includes a laser (IRL) 110, for example, including a near-IR or mid-IR laser emitting in the 2-5 µm wavelength range. The laser 110 may include, for example, a distributed feedback (DFB) laser diode in the near-infrared (near-IR) wavelength up to ~3 µm, a quantum cascade laser (QCL) in the mid-infrared (mid-IR) region beyond ~4 µm, or a GaSb-based interband cascade laser (ICL) emitting in the 3-4 µm wavelength range. Advantageous embodiments may make use of a commercially available ICL laser such as is available from Nanoplus Nanosystems and Technologies GmbH. An advantageous ICL has a small size and operates in a continuous wave (CW) at room temperature with low power requirements. The ICL may be tunable and may be advantageously configured to emit infrared radiation with a wavenumber in a range from about $2980 \text{ cm}^{-1}$ to about $2990 \text{ cm}^{-1}$ (e.g., from a wavenumber greater than or equal to about $2985 \text{ cm}^{-1}$ to a wavenumber less than or equal to about $2988 \text{ cm}^{-1}$ or from about $2986 \text{ cm}^{-1}$ to about $2987 \text{ cm}^{-1}$). As described in more detail below C12 and C13 ethane lines (absorption peaks) have been identified at a wavenumbers in a range from about $2986 \text{ cm}^{-1}$ to about $2987 \text{ cm}^{-1}$. These lines may be advantageously utilized to compute a C13 ethane to C12 ethane ratio in a gas sample.

In advantageous embodiments, a mid-IR laser beam emitted by an ICL passes through a dichroic mirror 120 and a beam mode matching lens 130 to a gas cell 150, such as a multipass gas cell (MPGC) or a hollow wave guide (HWG). The focal point of the lens 130 is positioned at an inlet port of the gas cell 150 for optimum power transfer from the ICL to the cell 150. The lens 130 may be configured to have substantially any suitable focal length, for example, in a range from about 100 to about 400 mm (such as about 200 mm). The laser beam may be directed by one or more plane mirrors 140a, 140b to the gas cell 150. While not required, the use of plane mirrors may enable the construction of a more compact instrument (by enabling the beam to traverse the focal length of lens 130 in a compact region).

The apparatus 100, 100' may make use of substantially any suitable gas cell 150, such as a MPGC. A MPGC is configured to enable the laser beam to make multiple passes through the gas cell and therefore the sample before exiting the cell. Advantageous MPGCs are generally compact and may include astigmatic mirrors that reflect the laser beam in the cell. In one example embodiment, the MPGC included a Herriot multi-pass gas cell having a path length of 10 m and a volume of 700 mL (available from Thorlabs, Inc.). In other example embodiments, the gas cell 150 may include a hollow wave guide (HWG), such as a low volume HWG. In such embodiments, the HWG may be a single pass or a multipass HWG. In certain advantageous embodiments, a suitable HWG may have a small cell volume, for example, having an inner diameter in a range from about 0.2 to 1 mm and a length in a range from about 0.2 to 10 m. The use of a small volume HWG may advantageously enable fast isotopic ethane measurements to be made using the disclosed embodiments.

Upon exiting the gas cell 150, the laser beam is received at an infrared sensor 170. In certain embodiments, the beam may be reflected off of a parabolic mirror 160 to focus the beam at the sensor 170. A suitable parabolic mirror may have substantially any suitable focal length, for example, from about 10 mm to about 100 mm (such as about 35 mm). The sensor may include substantially any suitable infrared sensor, for example, including a mercury-cadmium, telluride (MCT) detector.

While not limited in this regard, the depicted embodiment may include a temperature controller 112 programmed to control ICL temperature at a constant value such as 25° C. A current driver 114 may be configured to provide a low-noise current to the ICL. Although not depicted, the apparatus may further include a second temperature controller configured to control the temperature of the gas in the gas cell 150.

The gas cell 150 may include a gas inlet 151 and gas outlet 152 for receiving and expelling a gas sample. A pressure controller 155 and vacuum pump 157 may be configured to regulate the gas pressure in the cell. In general, it is desirable to make the measurements at low pressures, for example, at pressures less than about 100 mbar (such as about 10 mbar).

The apparatus 100' may further include a controller 190 (such as a desktop or laptop PC) configured to control the current driver and to receive and digitize the infrared sensor output. The controller may further include software configured to process the received sensor output to estimate (e.g., compute) the isotopic ratio of ethane in the gas sample. For example, the controller may be configured to identify first and second absorption peaks in the received sensor output and to process a ratio of those peaks to estimate at least a ratio of C13 ethane to C12 ethane in the gas sample.

Figure 4:
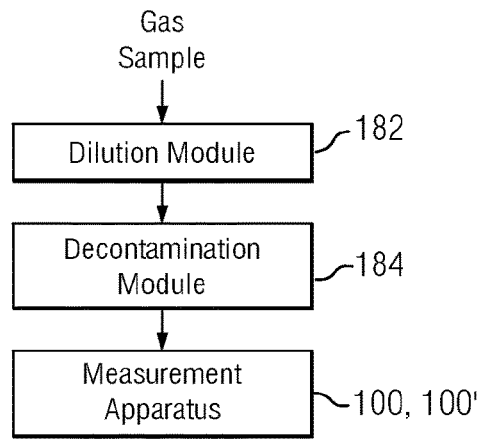
FIG. 4 depicts yet another example isotopic ratio measurement apparatus.

FIG. 4 depicts another example apparatus for making isotopic ethane measurements. The depicted example includes a dilution module 182 and a decontamination module 184 deployed upstream of one of the previously described apparatuses 100, 100'. The dilution module 182 may be configured to receive and dilute the gas sample (the formation gas acquired from the well). For example, the gas sample may be diluted with air or nitrogen such that the ethane concentration is in a range from about 100 ppm to about 1000 ppm.

In certain embodiments, the decontamination module 184 may be configured, for example, to remove hydrocarbons having three or more carbon atoms (e.g., C3, C4, C5, etc.). In such embodiments, the decontamination module may be configured to heat the gas in a catalysis oven (e.g., as disclosed in U.S. Pat. No. 9,671,381) to remove the larger hydrocarbons while retaining methane and ethane (C1 and C2). Light-off curves reported in the literature, using a commercial Pt—Rh/CeO2-Al2O3 catalyzer, show that the temperatures for 50% conversion were: methane, 515° C.>ethane, 435° C., 435° C.>propane, 290° C.>hexane for alkanes and acetylene, 285° C.>ethylene, 205° C. for alkenes. Dilution before catalysis combustion may be advantageous to limit HC concentrations (C2 (max): 100-1000 ppm) and extend the catalyzer lifetime. The decontamination module may additionally and/or alternatively include a molecular sieve to trap the larger hydrocarbons.

In embodiments that employ an HWG gas cell, the decontamination module 184 may advantageously include a gas chromatography (GC) column configured to separate the individual gas components in the gas sample. The use of a GC column may be enabled by the small volume of the HWG cell. In such embodiments, the gas sample may be diluted using the dilution module at 182 and then routed through the GC column 184 to obtain an ethane gas sample. The ethane gas sample may then be routed to the HWG gas cell 150 where it may be evaluated to estimate the ratio of C13 ethane to C12 ethane in the gas sample. Use of the HWG gas cell and GC column decontamination module may advantageously obviate the need to separate methane and ethane peaks in the IR measurements and may further enable fast isotopic ethane measurements.

Figure 5:
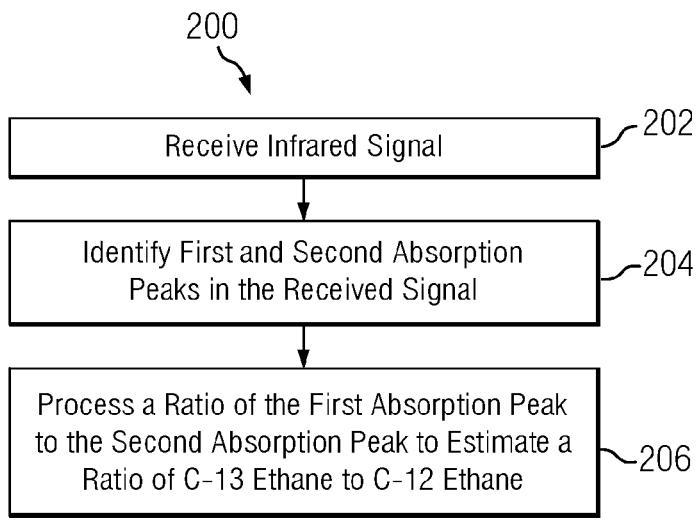
FIG. 5 depicts a flow chart of one example method for estimating an isotopic ratio of naturally occurring ethane.

FIG. 5 depicts a flow chart of one example method 200 for processing infrared sensor measurements to estimate an isotopic ratio of naturally occurring ethane. The infrared signal is received at 202, for example, using sensor 170 described above in FIGS. 2 and 3. The received signal is evaluated to identify first and second absorption peaks at 204, a ratio of which is in turn processed at 206 to estimate a ratio of C13 ethane to C12 ethane in the gas sample.

Figure 6:
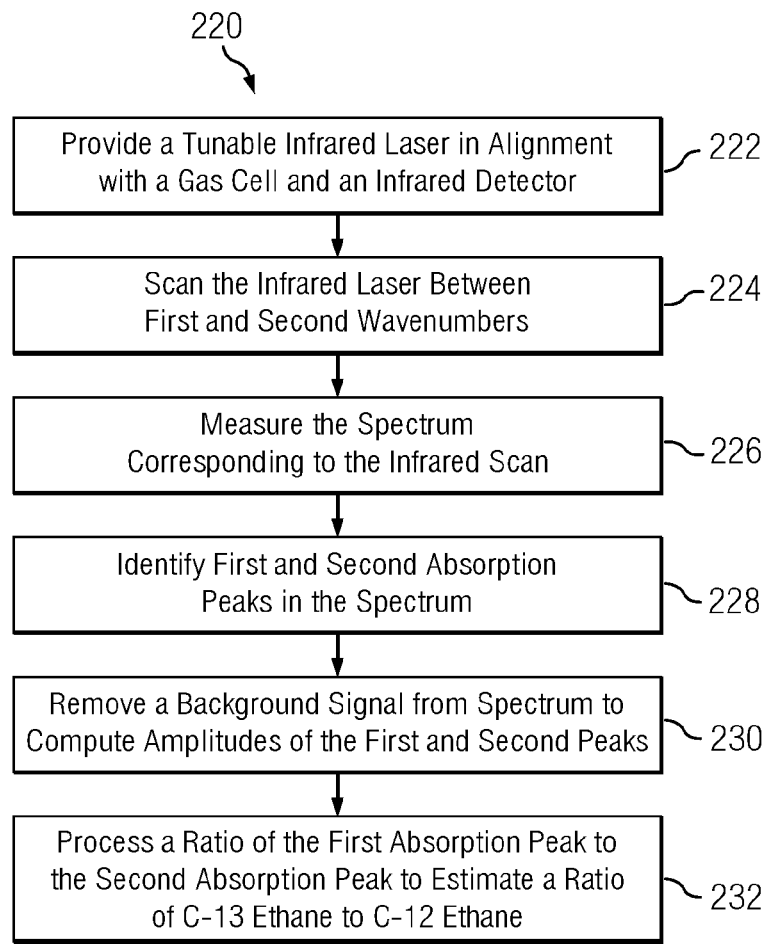
FIG. 6 depicts a flow chart of another example method for estimating an isotopic ratio of naturally occurring ethane.

FIG. 6 depicts a flow chart of another example method 220 for estimating an isotopic ratio of naturally occurring ethane. A tunable infrared laser is provided at 222 in alignment with a gas cell and an in infrared detector, for example, as described above with respect to FIGS. 2 and 3. A gas sample is introduced into the gas cell and the tunable infrared laser is wavelength scanned between first and second wavenumbers at 224 (e.g., between a first wavenumber of about 2986 cm$^{-1}$, such as 2986.2 cm$^{-1}$, and a second wavenumber of about 2987 cm$^{-1}$, such as 2987.3 cm$^{-1}$). Infrared radiation is measured (received) at the infrared detector and used to generate a spectrum at 226 corresponding to the wavenumber scan (the spectrum may include, for example, the measured IR intensity as a function of measurement number or wavenumber). The spectrum is evaluated to identify first and second absorption peaks therein at 228. The peaks may be identified, for example, based on the wavenumber of each peak (e.g., in a range from about 2986 cm$^{-1}$ to about 2987 cm$^{-1}$ such as about 2986.3 for the first peak and about 2986.7 for the second peak). The peaks may also be recognized based on a pattern recognition routine in which the relative positions of the first and second peaks and other peaks in the scan are recognized. The use of such pattern recognition routines is common in spectroscopy. After identifying the peaks, the peak amplitudes may be determined at 230 by removing the background signal from the spectrum (e.g., using techniques known to those of ordinary skill). A ratio of the peak amplitudes may be computed at 232 and used to estimate the ratio of C13 ethane to C12 ethane in the gas sample (e.g., a ratio of the second peak to the first peak).

With reference again to FIG. 3, one example apparatus used to make preliminary measurements is described in more detail. A CW, DFB ICL 110 from Nanoplus GmbH, Germany was packaged in a 5×5×5 cm TO66 assembly which included a thermoelectric cooler (TEC). The TEC and an MCT detector 170 (Vigo System S.A.) were configured with a preamplifier in a 40×81×40 mm footprint. A beam mode matching lens having a 200 mm focal length positioned at a MPGC inlet port was used to provide optimum power transfer from the ICL 110 to the MPGC 150.

While not required, an alignment diode laser ($\lambda$=630 nm) and a dichroic mirror (ISO optics, model BSP-DI-25-3) were utilized were to assist in the optical alignment of the MPGC 150 and the MCT detector 170. After the ICL beam and the visible alignment beam were aligned collinearly using the mirror, the combined beam was coupled into the MPGC using the mode matching lens 130. As depicted on FIG. 3, the plane mirrors, M1 and M2 (142, 144), changed the beam direction by 180 degrees to provide the required 200-mm distance for the mode matching lens, folding the optical path and reducing the size of the sensor optical core. The collimated ICL beam exiting the MPGC was focused onto the TEC, MCT detector using a 35 mm focal length parabolic mirror.

While not depicted, embodiments of the apparatus 100' may include an in-line reference cell located between the IR laser 110 and the dichroic mirror 120 (or the lens 130 in embodiments not employing a dichroic mirror). The reference cell may provide a reference signal to identify the laser wavelength in real time and to avert wavelength drift, when target gases are not present.

With continued reference to FIG. 3, the controller 190 may be configured to control an ICL temperature controller 112 and a current driver 114. To minimize laser frequency noise, a low-noise laser driver board developed may be selected (e.g., the ITC4002QCL available from Thorlabs). In example measurements described in more detail below, the ICL 110 was operated at a current of 57 mA and temperature of 25° C., which provided an optical power of ~8 mW. The pressure in the MPGC 150 was reduced to 10 mbar in order to avoid spectral overlap.

In the described example embodiment, the controller 190 further included a laptop equipped with a NI data acquisition (DAQ) card and a dual channel arbitrary function generator to generate a 500 Hz saw-tooth wave with a DC offset. The offset determined the ICL center wavelength, while the saw-tooth wave was used to scan the ICL wavelength center wavelength. The amplitude of the offset depended on the characterization of the ICL and the wavelength of the target absorption line. The laptop DAQ combination acquired the spectral data from the MTC detector with a sampling rate of 500 kS/s to 1000 kS/s.

The data processing was performed as follows. First, 500 spectra were averaged by ramping the laser current at 500 Hz to cover the targeted spectral region and collect the detector output using the DAQ. Every spectrum incorporated either 2000 or 8000 data points. In order to obtain the baseline of a spectral scan, the absorption peak was removed from the averaged spectrum. Subsequently, the remaining data points were fitted by means of a fifth order polynomial. On the basis of fitting the baseline, the absorbance was calculated, which was then linearized using the quadratic polynomial obtained in advance from the fringe spacing of a Ge etalon. Finally, a Voigt line shape (or simply Gaussian profile) was fitted to the linearized absorbance using a Levenberg-Marquardt least-squares fit procedure to retrieve the target gas concentrations. The output rate of the spectra output was 1 Hz.

FIGS. 7A and 7B (collectively FIG. 7) depict absorbance as a function of wavelength calculated and linearized by means of a 2.54 cm long Germanium etalon with a free spectral range (FSR) of 1.44 GHZ (7A) and a calibration model used to convert spectrum channels (or data points) to the corresponding wavenumbers (7B). A calibration curve based on a fifth-order polynomial regression was used to convert spectrum channels (or data points) to the corresponding wavenumbers.

A saw-tooth wave scan of the ICL current around the central current of 55 mA, resulted in wavelength tuning between 2986.2 cm$^{-1}$ to 2987.3 cm$^{-1}$. Since the saw-tooth signal was not registered to use the full DAQ bandwidth for spectrum sampling, the laser was switched-off systematically by setting the initial current below the laser threshold (~24 mA). A HITRAN simulation of methane was performed to confirm the initial wavelength assignment: 2986.2 cm$^{-1}$ and the etalon FSR. These parameters were fine-tuned to match the HITRAN simulation in particular the etalon FSR can change slightly as function of the ambient temperature. A typical 500-averaging (1 Hz acquisition rate) methane spectrum acquired from a known concentration level of 19% is depicted on FIG. 8 with the corresponding HITRAN simulation. The spectrum baseline was measured using zero air and subtracted from the raw methane transmission spectrum. A good agreement between the experimental (8B) and simulated (8A) spectra was observed.

While a good agreement between experimental and simulated spectra was observed for methane, it should be noted that ethane C13 absorption lines are not available in the HITRAN database in this spectral region (3.4 µm) and needed to be determined experimentally (as described below).

Figure 9A:
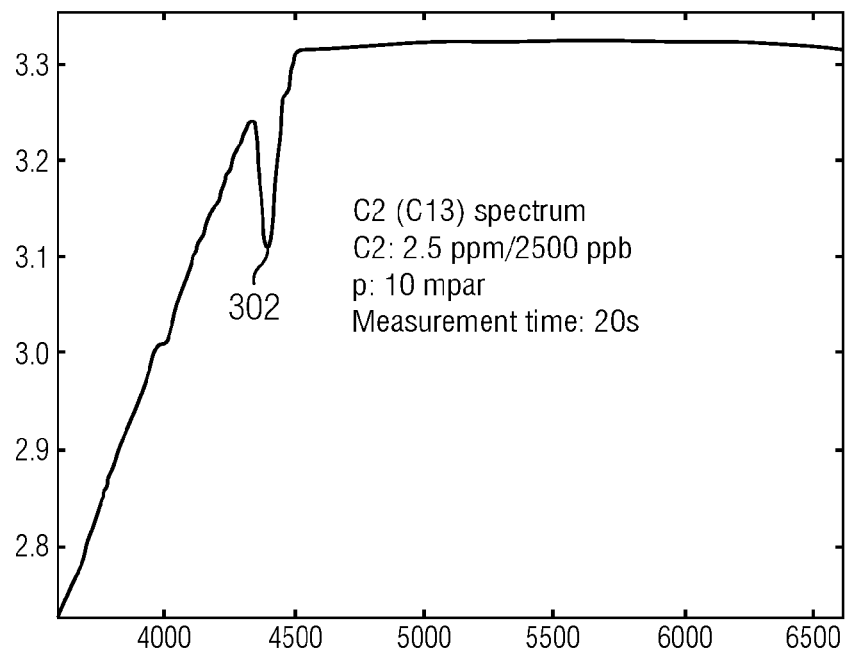
FIGS. 9A and 9B (collectively FIG. 9) depict a C13 ethane spectral line identification (9A) and a detection limit estimation (9B).
Figure 9B:
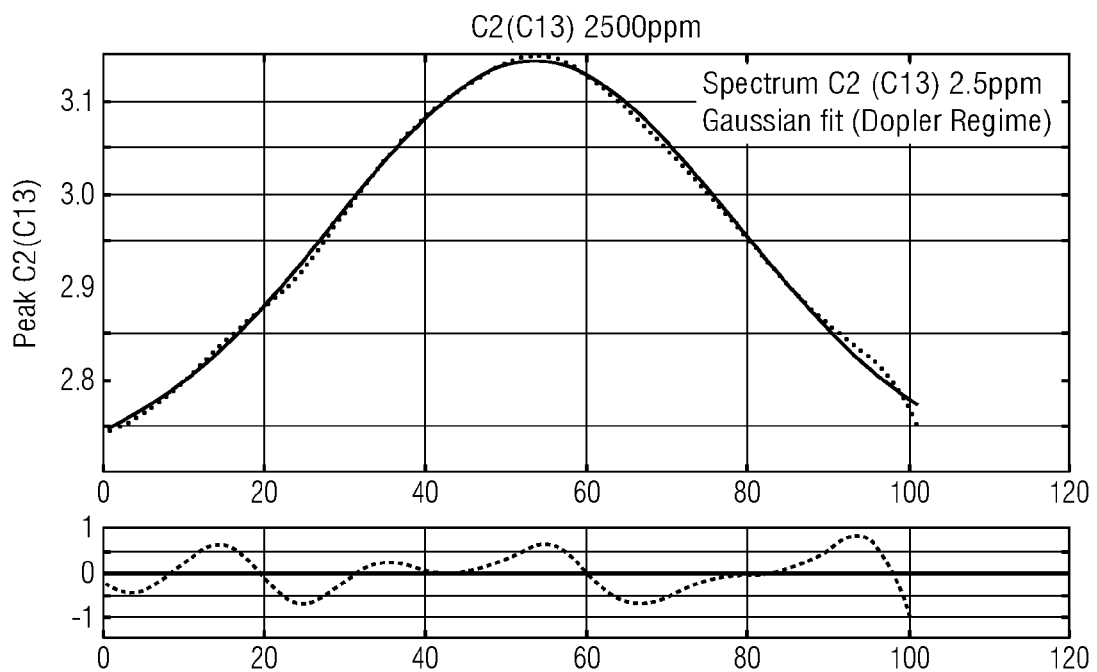

FIGS. 9A and 9B (collectively FIG. 9) depict a C13 ethane spectral line identification (9A) and a detection limit estimation (9B). An example C13 ethane absorption peak is shown at 302. In a previous study, IR absorption lines of the ethane isotopologues were measured for the first time in the mid IR range using an FTIR spectrometer. In this work, high-resolution absorption cross sections of the same isotopologues were measured with an ICL near 2986 cm$^{-1}$. Using an ethane C13 (100 ppm N2 balance gas) provided by CalGas/Air Liquid, diluted to 2500 ppb, the presence of a strong ethane C13 line near 2986.4 cm—was confirmed, as shown on FIG. 9.

The signal-to-noise ratio (SNR) is commonly defined as the ratio of the signal power to the background noise power and is often expressed in decibels (dB). In this work, the SNR was calculated as the highest possible absorption signal ($S_{max}$) of a specific substance divided by the standard deviation of the background signal during a nitrogen measurement: SNR=$S_{max}/(\sigma N2)$ where $\sigma N2$ was considered the noise level.

The LOD is specified as the lowest quantity/concentration of a substance that can be distinguished from the absence of that substance. The SNR can be used for the calculation of the LOD of a substance, for example as follows: LOD=c/SNR where c is the concentration of the substance during the SNR measurement. The obtained LOD is idealized, because it would be hard to distinguish a meaningful signal from the noise level, if both are of the same magnitude. Therefore, the value represents only a rough estimate of the experimentally achievable LOD. In order to measure the noise level of the above described apparatus, the MPGC was flushed with pure nitrogen and measurements were conducted under ambient temperature and a gas pressure of 10 mbar. The estimated LOD of the ethane C13 line was about 25 ppb corresponding to a SNR of 100 for ethane C13 sample with a concentration of 2500 ppb. The noise level was about $4 \times 10^{-4}$ RMS which is in agreement with the specifications provided by the manufacturer of the MPGC.

Figure 10:
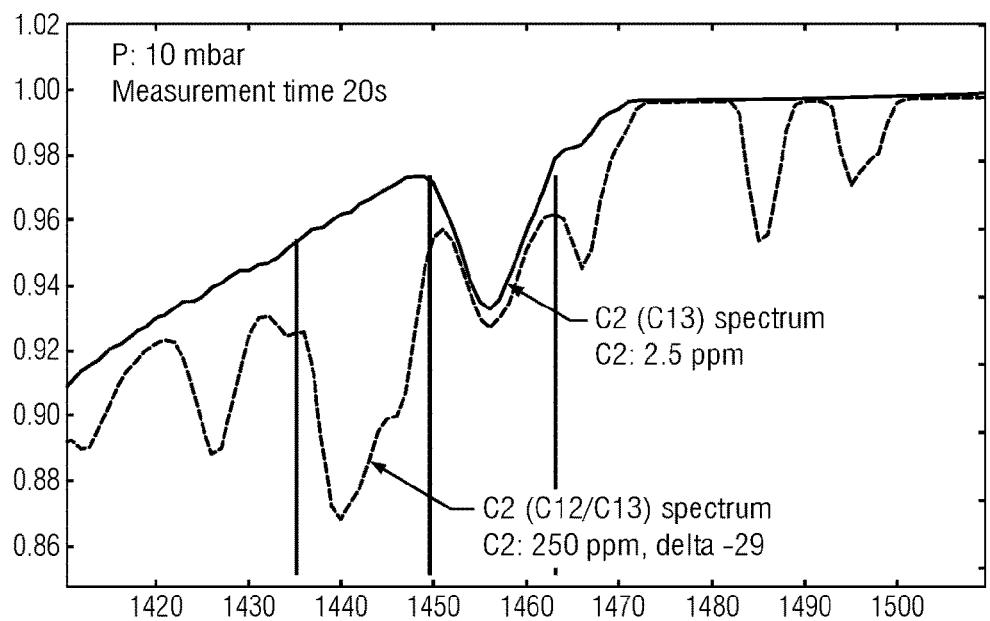
FIG. 10 depicts a C13 ethane spectrum (solid) and a standard C12 ethane (dashed) spectrum at wavenumbers of about 2986 to about 2987 cm$^{-1}$.

The amplitude of the identified C13 ethane peak matches the corresponding peak of a standard ethane sample at approximatively 250 ppm (~ 1% of the ethane C12 line reported in HITRAN at 2986.7 $cm^{-1}$) as shown in FIG. 10. It was estimated that interference between the ethane C13 and potential ethane C12 line are weak and can be corrected using an accurate calibration of ethane concentration. To experimentally determine an accurate estimation of ethane C12 absorption lines would require isolating the ethane C12 molecules. Nevertheless, this process is extremely expensive and never used in practice. An alternative approach would require an improvement of the current optical setup to remove the baseline spectrum using better optical component (i.e., neutral density) or a less sensitive infrared detector that do not saturate using about 8 mW optical power.

Figure 11A:
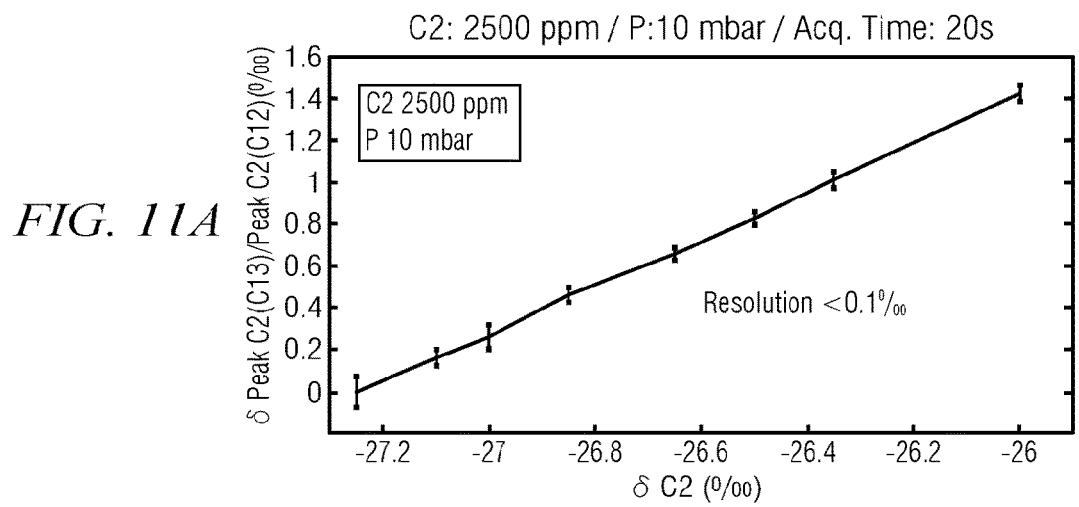
FIGS. 11A and 11B (collectively FIG. 11) depict peak ratio plots at high (11A) and low (11B) ethane gas concentrations.
Figure 11B:
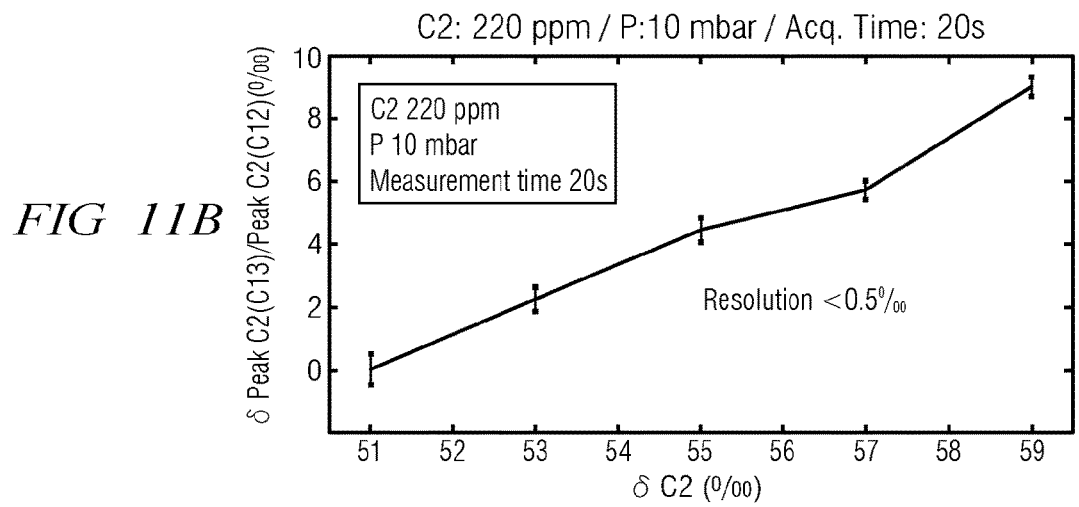

FIGS. 11A and 11B (collectively FIG. 11) depict peak ratio plots at high (11A) and low (11B) ethane gas concentrations. The isotope ratio (C13/C12) was calculated using the ratio between the peak maxima of C13 and C12 lines (as described above), as shown in FIG. 11, with a spectrum acquisition-time of 20s at a gas pressure of 10 mbar for two ethane concentrations: 2500 ppm and 220 ppm. As depicted on FIG. 11, the peak ratio (on the vertical axis) is approximately linear with respect to the isotopic ratio (on the horizontal axis).

To assess the linearity of the ethane isotopic ratio measurement, C13 ethane was progressively mixed (100 ppm) with a standard ethane sample (2500 ppm, delta ethane-29%). The measured variations of the isotope ratio (C13/C12) as function of the estimated isotope ratio are shown on FIG. 11. For the gas sample at high concentration (2500 ppm) (11A), a high sensitivity of delta ethane measurements: <0.1% % (delta resolution) and a good linearity ($R^2>0.9$) were achieved. For the gas sample at low concentration (220 ppm) (11B), a lower sensitivity <0.1% % (delta resolution) and a good linearity (R2>0.9) were achieved. The delta resolution was also confirmed with the uncertainty evaluation based on one-second standard deviation estimation (<0.1%). It should be noted that these measurements were performed at relatively stable ambient temperature (<1K) in a laboratory. Any temperature variation affecting the linearity of the isotopic measurement may be improved by controlling the temperature of the MPGC. Temperature variation of the gas cell is believed to be one of the most important parameters impacting the measurement drifts and it is commonly controlled to a better than 0.1° C. in commercial isotope analyzers. To better evaluate the required stability of the gas cell temperature, further experimental measurements are necessary, however, it will be understood that one of ordinary skill would readily be able to implement a temperature controller configured to control the temperature of the gas cell.

An Allan-Werle deviation analysis allows a determination of the amount of time the optical sensor signals can be averaged in order to improve the detection sensitivity. To assess the long-term stability, the ratio between the peak maxima of C13 and C12 absorption lines (peaks) depicted in FIG. 10 was calculated for an acquisition time of 20s at a gas pressure of 10 mbar. The calculated sensitivity limit as a function of integration time is plotted in FIG. 12 based on the Allan-Werle deviation.

Figure 12A:
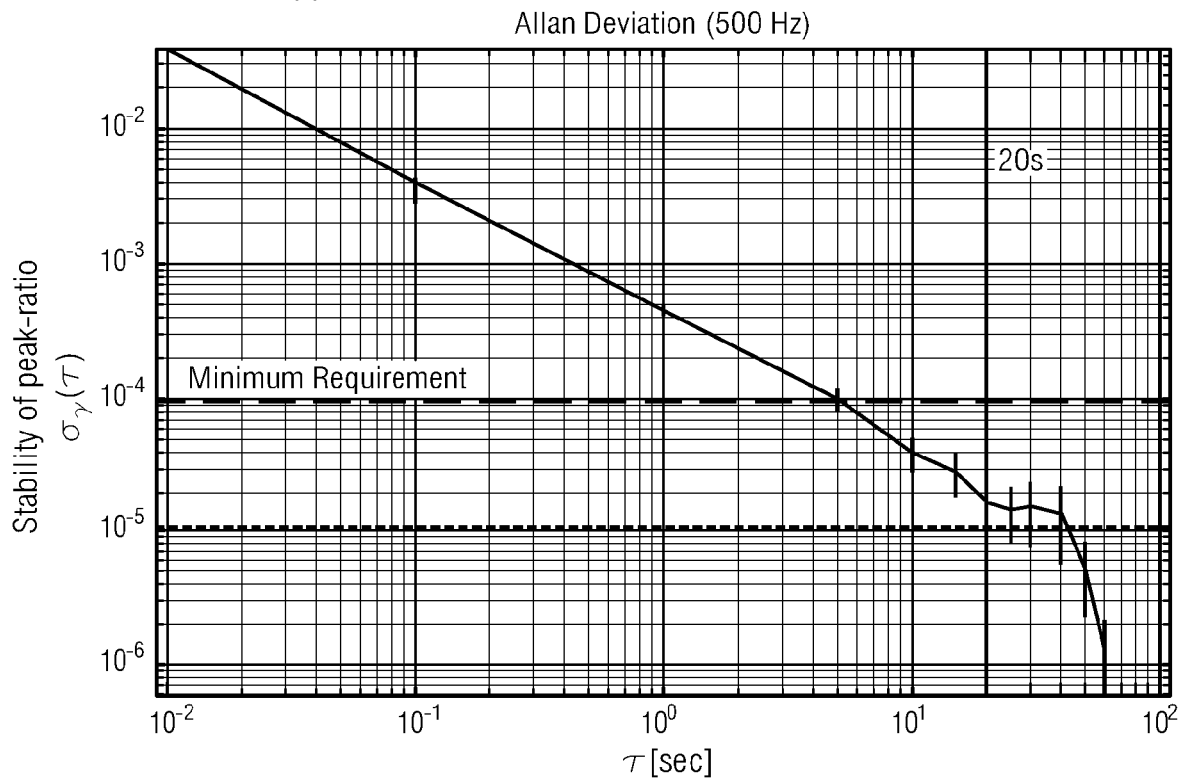
FIGS. 12A and 12B (collectively FIG. 12) depict Allan-Werle deviation analyses of the ethane isotopic ratios at the gas compositions shown in FIGS. 11A and 11B.
Figure 12B:
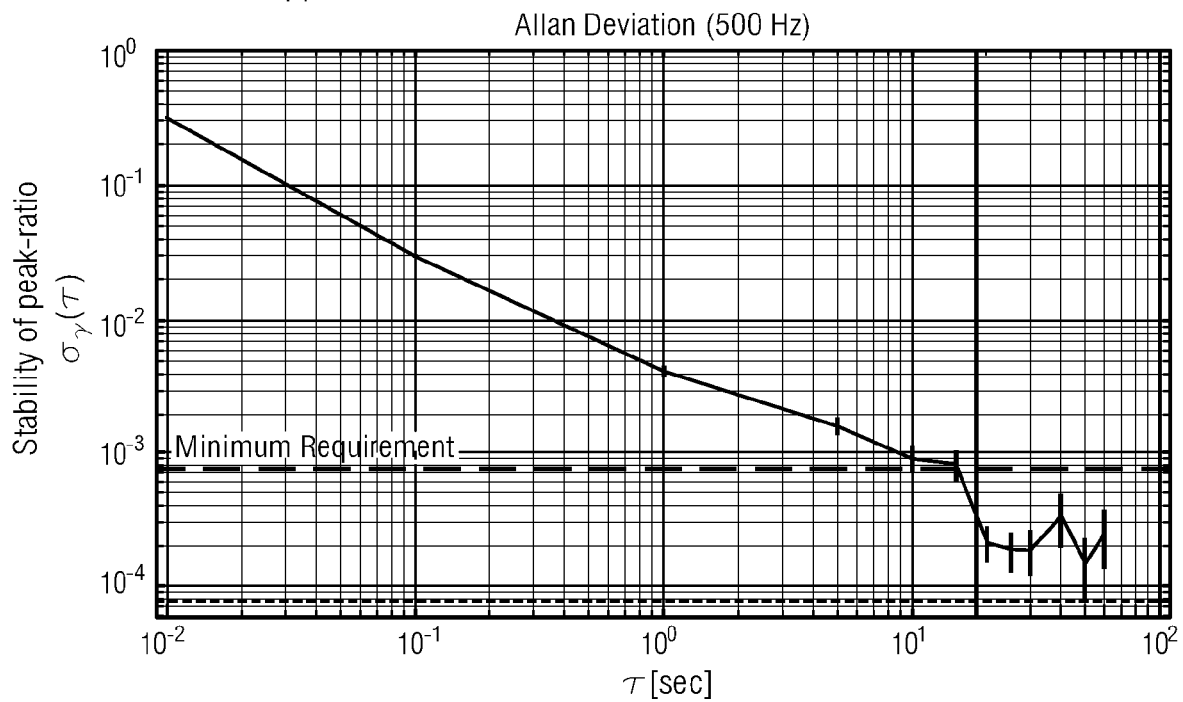

FIGS. 12A and 12B (collectively FIG. 12) depict Allan-Werle deviation analyses of the ethane isotopic ratios at the gas compositions shown in FIGS. 11A and 11B. Within an integration time of about 50 sec, the standard deviation decreased down to 0.1% % and 0.5% % for ethane high (2500 ppm) (12A) and low (220 ppm) (12B) concentrations, respectively. These results agree with the linearity and uncertainty analysis discussed previously. Based on the foregoing, it may be concluded that an isotopic ratio stability better than 0.5% % for a low ethane sample (200 ppm) may be achieved. To achieve a better performance at lower concentration, one may consider selecting a longer path length gas cell and increased gas pressure in the range (e.g., 20-50 mbar). The analyzer performances are mainly limited by the temperature drift in the lab and can be easily improved by controlling the temperature of the gas cell as noted above.

A feasibility study was performed using an optical bench (with many of the optical component being mounted on an optical bench) to simplify the control of optical components (laser, optics), electronics (laser driver), and gas conditions (flow, pressure and temperature) and to enable selection of the most suitable configuration for Isotopes analysis. Based on the theoretical analysis using HITRAN database and preliminary high-resolution FTIR measurements, an ICL light source was selected at wavelength centered around 2986 $cm^{-1}$ (3.349 mm). The experimental results confirmed the spectral information (position and strength) of the C13 line of ethane near 2986 $cm^{-1}$. It was also demonstrated that there is limited interference between minor C12 and C13 absorption lines in this spectral region. Despite the lack of published data about ethane spectra in this spectral region, it was demonstrated for the first time that it may be possible to measure ethane isotope variation directly without the need of complex laboratory setup based on GC-IRM.

In the foregoing disclosure, it has been demonstrated that the C13 ethane to C12 ethane ratio may be determined for a substantially pure ethane composition (i.e., without significant interference from other hydrocarbons in the gas). As described above, hydrocarbons having three or more carbon atoms may be removed from the gas sample. The following analysis demonstrates that the presence of methane in the gas composition is not expected to significantly interfere with the ethane isotopic ratio measurements.

The spectrum of ethane is available in the literature with sufficient resolution but this this is not the case for ethane with isotope C13. We therefore chose to collect these two spectra (C12 and C13) to have two easily comparable spectra. Moreover, the ethane spectra for C12 is partially available in HITRAN database, as only strong lines are reported in the 3-4 μm region. It was observed that the spectrum of ethane C13 is similar in appearance to that of C12 with on average a shift of the peaks 0.4-0.8 $cm^{-1}$ towards the weak waves for C13 ethane. As infrared lasers (QCL or ICL) are generally tunable over a few wavenumbers (1-4 $cm^{-1}$), both isotopes may therefore advantageously be detectable with a single laser.

In general, absorption peaks tend to widen when the gas pressure increases owing to molecular collisions in the gas cell. For example, the peaks may widen slightly to reach 0.5 $cm^{-1}$ to 1 $cm^{-1}$ in width at half height. To distinguish the isotopic absorption peaks using a single laser, it may be advantageous to reduce the gas pressure in the cell to less than 100 mbar.

Figure 13:
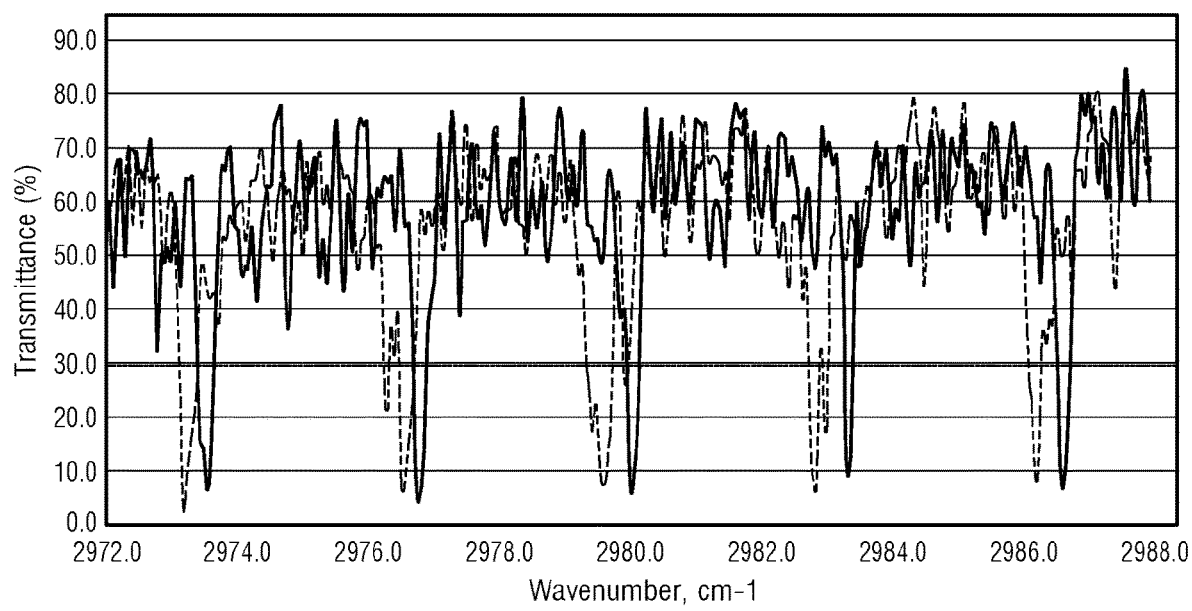
FIG. 13 depicts C12 and C13 ethane spectra acquired by high resolution FTIR at low pressure (10 mbar) in which C12 ethane is dashed, C13 ethane is solid, and ambient air is dotted.

With reference to spectra shown on FIG. 13, it is noted that the C13 ethane peaks are often split, possibly due to the substitution of only one carbon C13 atom in the ethane molecule. Roto-vibrational lines therefore have their frequencies slightly modified as a function of the proximity of a C12 or C13 carbon atom. This is not visible on standard ethane spectrum because the proportion of C13 is low. A peak attributable specifically to C13 ethane present in standard ethane is sometimes visible in the previous figures (2986 cm$^{-1}$ for example). The peaks in this region are intense and no very intense peaks of water are visible. As described above, the ICL laser depicted on FIG. 3 emits infrared radiation in this spectral region.

Figure 14:
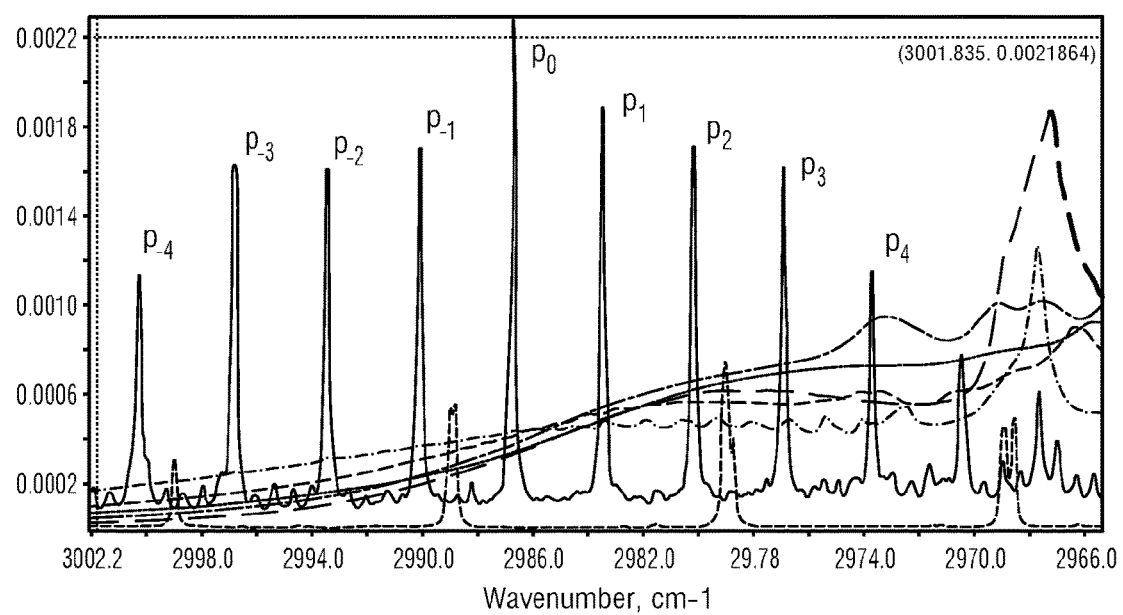
FIG. 14 depicts Pacific Northwest National Laboratory (PNNL) Fourier Transform Infrared (FTIR) spectra of light hydrocarbons.

Similar FTIR spectra for Ethane are collected and distributed by Pacific Northwest National Laboratory (PNNL) are shown in FIG. 14. The infrared spectra of light hydrocarbons (C1-C5) at high resolution are also shown. As shown, the ethane lines do not interfere with methane and hydrocarbon lines. However, a variation in baseline level may be anticipated in the case of presence of high hydrocarbon concentration in the gas sample (>1000 ppm) that can affect the isotope measurement precision. Ethane lines are separated by 3.3 cm$^{-1}$ and have symmetrical distribution around the central line at 2986 cm$^{-1}$ (refereed here as 'p0' for C2-C12 and 'q0' for C2-C13 line). The major C2 lines in this spectral region are referenced (p1, p2, etc.) according to their position compared to the central line (p0).

Due to low concentration of C13 Ethane (ppb level) and high methane concentration (percent level), ultra-high resolution spectra are required to study overlaps between ethane and methane minor lines that are not captured in FTIR data. Methane absorption lines are documented in detail in HITRAN database and so spectra with ultra-high resolution (<0.001 cm$^{-1}$) at low pressure (10 mbar) can be simulated. HITRAN simulation for ethane (C12), Methane (C12 and C13) lines at P=10 mbar and wavelength: 2986 cm$^{-1}$ are shown in FIG. 15.

Figure 15A:
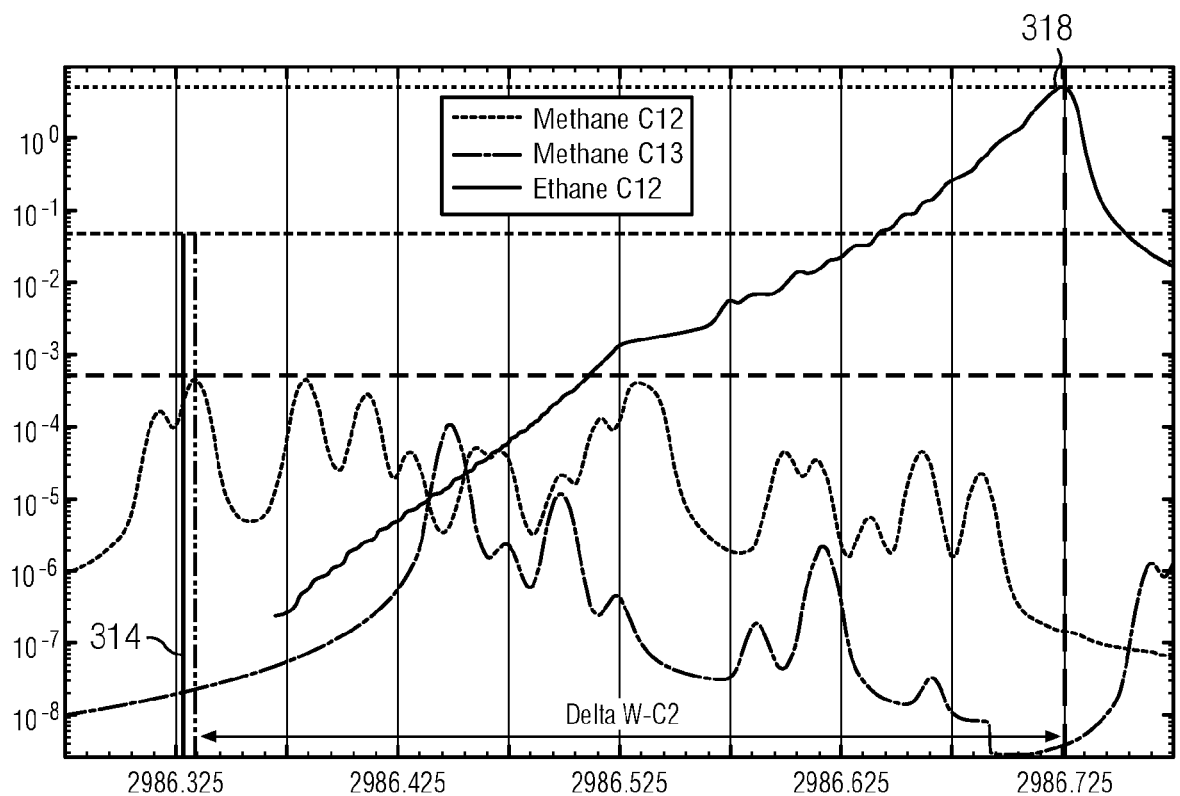
FIGS. 15A and 15B (collectively FIG. 15) depict a high-resolution transmission molecular absorption (HITRAN) simulation for Ethane (C12) and Methane (C12 and C13) lines at a pressure of 10 mbar and wavenumber 2986 cm$^{-1}$ (15A) and a position of the C13 ethane line relative to the C12 ethane line estimated based on FTIR data (15B).
Figure 15B:
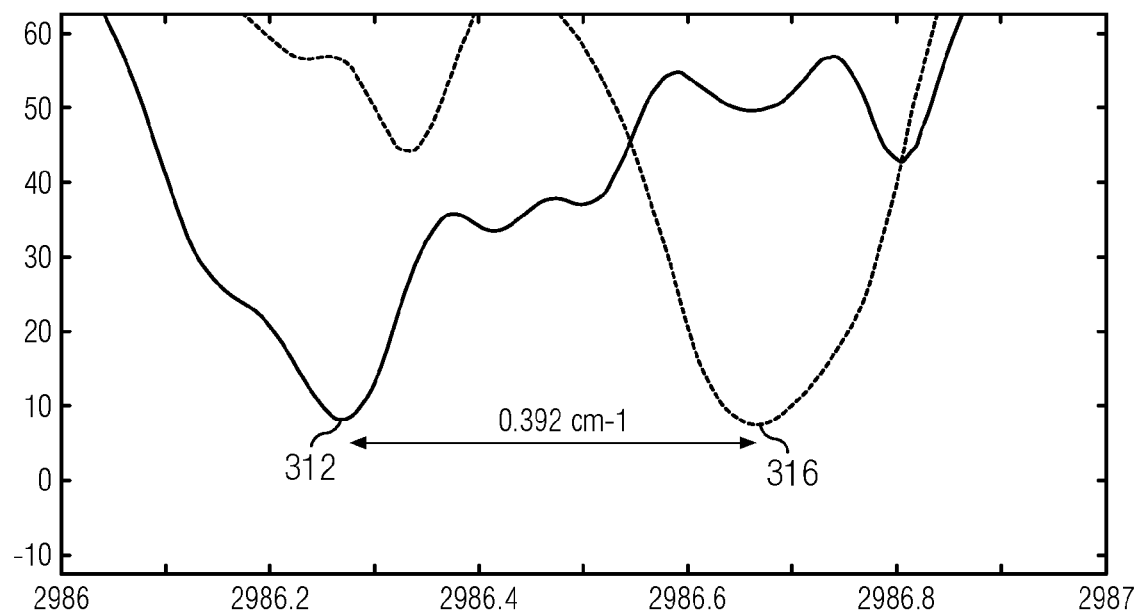

FIGS. 15A and 15B (collectively FIG. 15) depict a high-resolution transmission molecular absorption (HITRAN) simulation for Ethane (C12) and Methane (C12 and C13) lines at a pressure of 10 mbar and wavenumber 2986 cm$^{-1}$ (15A) and a position of the C13 ethane line relative to the C12 ethane line estimated based on FTIR data (15B). The position of Ethane C13 line relative to ethane C12 line is estimated based on FTIR data (0.392 cm$^{-1}$). The strength of the C13 ethane peak is calculated based on the strength of the corresponding C12 ethane line and its natural abundance (~1%). In FIG. 15B, an example C13 ethane peak 312 is observed at about 2986.3 cm$^{-1}$ (e.g., between 2986.2 cm$^{-1}$ and 2986.4 cm$^{-1}$) and corresponds to the line 314 in FIG. 15A. An example C12 ethane peak 316 is observed at about 2986.7 cm$^{-1}$ (e.g., between 2986.6 cm 1 and 2986.8 cm$^{-1}$) and corresponds to the ethane peak 318 in FIG. 15A. A ratio of ethane C13 to the overlapping methane line may be calculated and referred to as a methane rejection ratio. This ratio is estimated to be 100 for the central ethane lines (p0) at 2986 cm$^{-1}$.

In order to reach the required measurement precision (1% ‰), this ratio may be higher than 1000 in case of similar ethane and methane concentration in the sample. However, a ratio between 100-1000 between C1 and C2 is frequently encountered in natural gas samples. In this case, a methane rejection ratio on the order of $10^5$ is desirable.

Figure 16A:
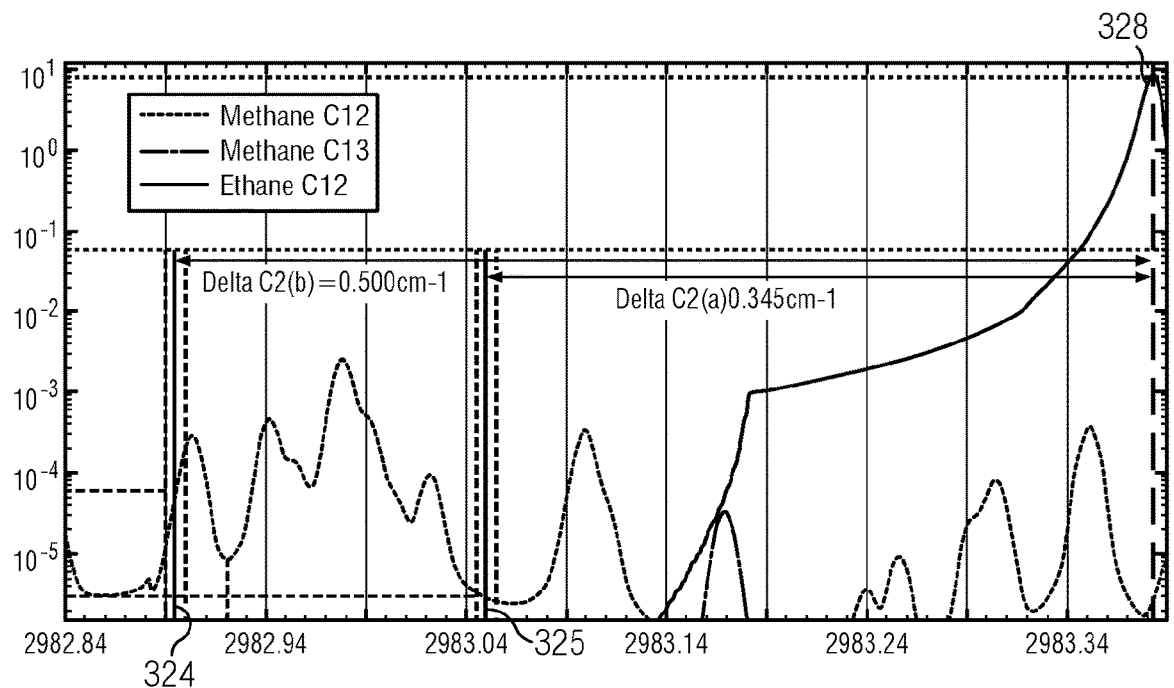
FIGS. 16A and 16B (collectively FIG. 16) depict a HITRAN simulation for Ethane (C12) and Methane (C12 and C13) lines at a pressure of mbar and wavenumber 2983 cm$^{-1}$ (16A) and a position of the C13 ethane line relative to the C12 ethane line estimated based on FTIR data (16B).
Figure 16B:
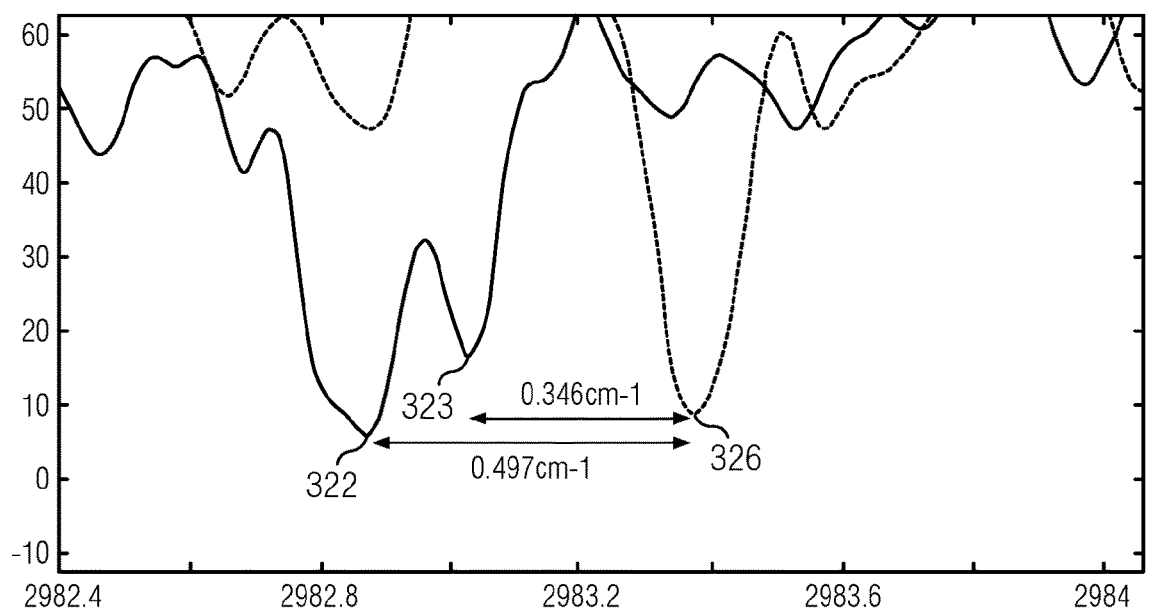

FIGS. 16A and 16B (collectively FIG. 16) depict a HITRAN simulation for Ethane (C12) and Methane (C12 and C13) lines at a pressure of mbar and wavenumber 2983 cm$^{-1}$ (16A) and a position of the C13 ethane line relative to the C12 ethane line estimated based on FTIR data (16B). As shown in FIG. 16, the highest methane rejection ratio in this spectral region is about $10^4$ for the ethane line (p$^{-1}$) at the wavelength 2983 cm$^{-1}$. In this case, an accurate calibration of methane is required at high concentration to correct of it effect on C2 isotope ratio. The methane rejection ratios of the remaining ethane lines were estimated to be lower than 103. In FIG. 16B, example C13 ethane peaks 322, 323 are observed at 2982.9 cm$^{-1}$ (e.g., between 2982.8 cm$^{-1}$ and 2983.0 cm$^{-1}$) and 2983.0 cm$^{-1}$ (e.g., between 2982.9 cm$^{-1}$ and 2983.1 cm$^{-1}$) and correspond to the lines 324, 325 in FIG. 16A. An example C12 ethane peak 326 is observed at 2983.4 cm$^{-1}$ (e.g., between 2983.3 cm$^{-1}$ and 2983.5 cm$^{-1}$) and corresponds to the C12 ethane peak 328 in FIG. 16A.

As noted above, the feasibility of determining a ratio of C13 ethane to C12 ethane in naturally occurring formation gas has been demonstrated. The disclosed apparatus and method advantageously simplify the control of optical components (laser, optics), electronics (laser driver), and gas conditions (flow, pressure and temperature) and to enable selection the most suitable configuration for Isotopes analysis. Based on the theoretical analysis using the HITRAN database and preliminary high-resolution FTIR measurements, an ICL light source was selected at wavelength centered around 2986 cm$^{-1}$. The experimental results disclosed herein confirm the spectral information (position and strength) of the C13 line of ethane near 2986 cm$^{-1}$. The use of this spectral line for a direct analysis of isotopic ethane ratio was also demonstrated. Despite the lack of published data about ethane spectrum in this spectral region, it has been demonstrated for the first time that ethane isotope variation can be measured directly without the need of complex laboratory setup based on GC-IRMS.

It will be understood that the present disclosure includes numerous embodiments. These embodiments include, but are not limited to, the following embodiments.

In a first embodiment, an apparatus for making isotopic ethane measurements of a gas sample comprises a tunable infrared laser configured to emit an infrared laser beam; an infrared sensor configured to receive the infrared laser beam; a gas cell deployed in a path between the tunable infrared laser and the infrared sensor such that the infrared laser beam passes through the gas cell, the gas cell configured to receive the gas sample via a gas inlet and expel the gas sample via a gas outlet; and a controller configured to evaluate the received infrared laser beam to estimate at least a ratio of C13 ethane to C12 ethane in the gas sample.

A second embodiment may include the first embodiment, wherein the gas cell comprises a hollow wave guide gas cell having an inner diameter in a range from 0.2 mm to 1 mm and a length in a range from 0.2 m to 10 m.

A third embodiment may include the second embodiment, further comprising a gas chromatography column configured to isolate an ethane sample from the gas sample and inject the ethane sample into the hollow wave guide.

A fourth embodiment may include any one of the first through third embodiments, wherein the tunable infrared laser comprises a continuous wave GaSb based interband cascade laser (ICL) configured to emit the infrared laser beam; and the infrared sensor comprises a mercury cadmium telluride (MCT) infrared detector configured to receive the infrared laser beam.

A fifth embodiment may include the fourth embodiment, wherein the tunable infrared laser is configured to scan the emitted infrared laser beam from a first wavenumber greater than or equal to 2985 cm$^{-1}$ to a second wave number less than or equal to 2988 cm$^{-1}$.

A sixth embodiment may include any one of the first through fifth embodiments, further comprising a beam mode matching lens deployed in the path between the tunable infrared laser and the gas cell such that a focal point of the beam mode matching lens is located at the gas inlet of the gas cell.

A seventh embodiment may include any one of the first through sixth embodiments, further comprising a parabolic mirror deployed in the path between the gas cell and the infrared sensor, the parabolic mirror configured to focus the infrared laser beam exiting the gas cell onto the infrared sensor.

An eighth embodiment may include any one of the first through seventh embodiments, further comprising at least one of a temperature controller configured to control a temperature of the tunable infrared laser; and a pressure controller configured to control a pressure of the gas sample in the gas cell.

A ninth embodiment may include any one of the first through eighth embodiments, further comprising at least one of a dilution module configured to dilute the gas sample with air or nitrogen such that an ethane concentration in the gas sample is in a range from about 100 ppm to about 1000 ppm; and a decontamination module configured to remove hydrocarbons having three or more carbon atoms from the gas sample.

A tenth embodiment may include any one of the first through ninth embodiments, wherein the controller is further configured to cause the tunable infrared laser to scan the emitted infrared laser beam between first and second wavenumbers; cause the infrared sensor to measure a spectrum corresponding to the scanned infrared laser beam; identify a first C13 ethane absorption peak and a second C12 ethane absorption peak in the measured spectrum; compute first and second amplitudes of the corresponding first and second absorption peaks by removing a spectral background; and compute a ratio of the first and second amplitudes to estimate the ratio of C13 ethane to C12 ethane in the gas sample.

In an eleventh embodiment, a method for making isotopic ethane measurements of a gas sample comprises introducing the gas sample into a gas cell, the gas cell deployed in a path between a tunable infrared laser and an infrared sensor, the tunable infrared laser configured to emit an infrared laser beam that passes through the gas cell and is received at an infrared sensor; scanning the emitted infrared laser beam between first and second wavenumbers; measuring a spectrum corresponding to the scanned infrared laser beam; identifying a first C13 ethane absorption peak and a second C12 ethane absorption peak in the measured spectrum; computing first and second amplitudes of the first and second absorption peaks by removing a spectral background; and computing a ratio of the first and second amplitudes to estimate a ratio of C13 ethane to C12 ethane in the gas sample.

A twelfth embodiment may include the eleventh embodiment, wherein the first wavenumber is greater than or equal to 2985 $cm^{-1}$ and the second wavenumber is less than or equal to 2988 $cm^{-1}$.

A thirteenth embodiment may include the twelfth embodiment, wherein the first C13 ethane absorption peak is at a wavenumber between 2986.2 $cm^{-1}$ and 2986.4 $cm^{-1}$ and the second C12 ethane absorption peak is at a wavenumber between 2986.6 $cm^{-1}$ and 2986.8 $cm^{-1}$.

A fourteenth embodiment may include any one of the eleventh through thirteenth embodiments, wherein the introducing comprises introducing the gas sample into a gas cell comprising a hollow wave guide having an inner diameter in a range from 0.2 mm to 1 mm and a length in a range from 0.2 m to 10 m.

A fifteenth embodiment may include any one of the eleventh through fourteenth embodiments, wherein the introducing comprises introducing the gas sample into a dilution module to obtain a diluted gas sample comprising from about 100 ppm to about 1000 ppm ethane; injecting the diluted gas sample into a gas chromatography column to isolate an ethane sample; and introducing the ethane sample into a gas cell comprising a hollow wave guide having an inner diameter in a range from 0.2 mm to 1 mm and a length in a range from 0.2 m to 10 m.

In a sixteenth embodiment, an apparatus for making isotopic ethane measurements of a gas sample comprises a tunable infrared laser configured to emit an infrared laser beam; an infrared sensor configured to receive the infrared laser beam; a gas chromatography column configured to isolate an ethane gas sample from the gas sample; a hollow wave guide deployed in a path between the tunable infrared laser and the infrared sensor such that the infrared laser beam passes through the hollow wave guide, the hollow wave guide configured to receive the ethane gas sample via a gas inlet and expel the ethane gas sample via a gas outlet, the hollow wave guide having an inner diameter in a range from 0.2 mm to 1 mm and a length in a range from 0.2 m to 10 m; and a controller configured to process a ratio of a first absorption peak to a second absorption peak in the received infrared laser beam to estimate a ratio of C13 ethane to C12 ethane in the gas sample.

A seventeenth embodiment may include the sixteenth embodiment, wherein the tunable infrared laser comprises a continuous wave GaSb based interband cascade laser (ICL) configured to emit an infrared laser beam; and the infrared sensor comprises a mercury cadmium telluride (MCT) infrared detector configured to receive the infrared laser beam.

An eighteenth embodiment may include the seventeenth embodiment, wherein the tunable infrared laser is configured to scan the emitted infrared laser beam from a first wavenumber greater than or equal to 2985 $cm^{-1}$ to a second wave number less than or equal to 2988 $cm^{-1}$.

A nineteenth embodiment may include any one of the sixteenth through eighteenth embodiments, further comprising a beam mode matching lens deployed in the path between the tunable infrared laser and the hollow wave guide such that a focal point of the beam mode matching lens is located at the gas inlet; and a parabolic mirror deployed in the path between the hollow wave guide and the infrared sensor, the parabolic mirror configured to focus the infrared laser beam exiting the hollow wave guide onto the infrared sensor.

A twentieth embodiment may include any one of the sixteenth through nineteenth embodiments, wherein the controller is further configured to cause the tunable infrared laser to scan the emitted infrared laser beam between a first wavenumber greater than or equal to 2985 $cm^{-1}$ to a second wavenumber less than or equal to 2988 $cm^{-1}$; cause the infrared sensor to measure a spectrum corresponding to the scanned infrared laser beam; identify a first C13 ethane absorption peak and a second C12 ethane absorption peak in the measured spectrum; compute first and second amplitudes of the corresponding first and second absorption peaks by removing a spectral background; and compute a ratio of the first and second amplitudes to estimate the ratio of C13 ethane to C12 ethane in the gas sample.

Although tunable laser spectroscopy measurement of C13 ethane has been described in detail, it should be understood that various changes, substitutions and alternations can be made herein without departing from the spirit and scope of the disclosure as defined by the appended claims.

The invention claimed is:

1. An apparatus for making isotopic ethane measurements of a gas sample, the apparatus comprising:

a tunable infrared laser configured to emit an infrared laser beam;
an infrared sensor configured to receive the infrared laser beam;
a gas cell deployed in a path between the tunable infrared laser and the infrared sensor such that the infrared laser beam passes through the gas cell, the gas cell configured to receive the gas sample via a gas inlet and expel the gas sample via a gas outlet; and
a controller configured to evaluate the received infrared laser beam to estimate at least a ratio of C13 ethane to C12 ethane in the gas sample, wherein the controller is further configured to:
cause the tunable infrared laser to scan the emitted infrared laser beam between first and second wavenumbers;
cause the infrared sensor to measure a spectrum corresponding to the scanned infrared laser beam;
identify a first C13 ethane absorption peak and a second C12 ethane absorption peak in the measured spectrum;
compute first and second amplitudes of the corresponding first and second absorption peaks by removing a spectral background; and
compute a ratio of the first and second amplitudes to estimate the ratio of C13 ethane to C12 ethane in the gas sample.

2. The apparatus of claim 1, wherein the gas cell comprises a hollow wave guide gas cell having an inner diameter in a range from 0.2 mm to 1 mm and a length in a range from 0.2 m to 10 m.

3. The apparatus of claim 2, further comprising a gas chromatography column configured to isolate an ethane sample from the gas sample and inject the ethane sample into the hollow wave guide.

4. The apparatus of claim 1, wherein:
the tunable infrared laser comprises a continuous wave GaSb based interband cascade laser (ICL) configured to emit the infrared laser beam; and
the infrared sensor comprises a mercury cadmium telluride (MCT) infrared detector configured to receive the infrared laser beam.

5. The apparatus of claim 4, wherein the tunable infrared laser is configured to scan the emitted infrared laser beam from a first wavenumber greater than or equal to 2985 cm$^{-1}$ to a second wave number less than or equal to 2988 cm$^{-1}$.

6. The apparatus of claim 1, further comprising a beam mode matching lens deployed in the path between the tunable infrared laser and the gas cell such that a focal point of the beam mode matching lens is located at the gas inlet of the gas cell.

7. The apparatus of claim 1, further comprising a parabolic mirror deployed in the path between the gas cell and the infrared sensor, the parabolic mirror configured to focus the infrared laser beam exiting the gas cell onto the infrared sensor.

8. The apparatus of claim 1, further comprising at least one of:
a temperature controller configured to control a temperature of the tunable infrared laser; and
a pressure controller configured to control a pressure of the gas sample in the gas cell.

9. The apparatus of claim 1, further comprising at least one of:
a dilution module configured to dilute the gas sample with air or nitrogen such that an ethane concentration in the gas sample is in a range from about 100 ppm to about 1000 ppm; and
a decontamination module configured to remove hydrocarbons having three or more carbon atoms from the gas sample.

10. A method for making isotopic ethane measurements of a gas sample, the method comprising:
introducing the gas sample into a gas cell, the gas cell deployed in a path between a tunable infrared laser and an infrared sensor, the tunable infrared laser configured to emit an infrared laser beam that passes through the gas cell and is received at an infrared sensor;
scanning the emitted infrared laser beam between first and second wavenumbers;
measuring a spectrum corresponding to the scanned infrared laser beam;
identifying a first C13 ethane absorption peak and a second C12 ethane absorption peak in the measured spectrum;
computing first and second amplitudes of the first and second absorption peaks by removing a spectral background; and
computing a ratio of the first and second amplitudes to estimate a ratio of C13 ethane to C12 ethane in the gas sample.

11. The method of claim 10, wherein the first wavenumber is greater than or equal to 2985 cm 1 and the second wavenumber is less than or equal to 2988 cm$^{-1}$.

12. The method of claim 11, wherein the first C13 ethane absorption peak is at a wavenumber between 2986.2 cm$^{-1}$ and 2986.4 cm$^{-1}$ and the second C12 ethane absorption peak is at a wavenumber between 2986.6 cm$^{-1}$ and 2986.8 cm$^{-1}$.

13. The method of claim 10, wherein the introducing comprises introducing the gas sample into a gas cell comprising a hollow wave guide having an inner diameter in a range from 0.2 mm to 1 mm and a length in a range from 0.2 m to 10 m.

14. The method of claim 10, wherein the introducing comprises:
introducing the gas sample into a dilution module to obtain a diluted gas sample comprising from about 100 ppm to about 1000 ppm ethane;
injecting the diluted gas sample into a gas chromatography column to isolate an ethane sample; and
introducing the ethane sample into a gas cell comprising a hollow wave guide having an inner diameter in a range from 0.2 mm to 1 mm and a length in a range from 0.2 m to 10 m.

* * * * *